(12) United States Patent
Thompson

(10) Patent No.: US 12,076,272 B2
(45) Date of Patent: *Sep. 3, 2024

(54) CONJUNCTIVAL COVER AND METHODS THEREFOR

(71) Applicant: TearOptix, Inc., Menlo Park, CA (US)

(72) Inventor: Vance M. Thompson, Sioux Falls, SD (US)

(73) Assignee: TearOptix, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/142,699

(22) Filed: May 3, 2023

(65) Prior Publication Data

US 2023/0404798 A1    Dec. 21, 2023

Related U.S. Application Data

(63) Continuation of application No. 17/376,686, filed on Jul. 15, 2021, now Pat. No. 11,672,698, which is a continuation of application No. 16/777,358, filed on Jan. 30, 2020, now Pat. No. 11,076,985, which is a continuation of application No. 15/827,582, filed on Nov. 30, 2017, now Pat. No. 10,548,767, which is a continuation of application No. 15/608,503, filed on May 30, 2017, now Pat. No. 10,449,086, which is a continuation of application No. 14/071,240, filed on Nov. 4, 2013, now Pat. No. 9,668,916.

(51) Int. Cl.
*A61K 9/00* (2006.01)
*A61F 9/00* (2006.01)

(52) U.S. Cl.
CPC .......... *A61F 9/0017* (2013.01); *A61K 9/0051* (2013.01)

(58) Field of Classification Search
CPC ...................................................... A61F 9/0017
See application file for complete search history.

(56) References Cited

U.S. PATENT DOCUMENTS

| 2,641,161 | A | 6/1953 | Silvertstein |
| 3,246,941 | A | 4/1966 | Moss |
| 3,416,530 | A | 12/1968 | Ness |
| 3,594,074 | A | 7/1971 | Rosen |
| 3,973,838 | A | 8/1976 | Page |
| 3,995,635 | A | 12/1976 | Higuchi et al. |
| 4,157,864 | A | 6/1979 | Koller et al. |

(Continued)

FOREIGN PATENT DOCUMENTS

| CA | 2539395 A1 | 4/2005 |
| EP | 0042679 A2 | 12/1981 |

(Continued)

OTHER PUBLICATIONS

Alverez-Lorenzo, Carmen, et al., "Contact Lenses for Drug Delivery: Achieving Sustained Release with Novel Systems", 2006, Am J Drug Deliv 2006;4(3): 131-151.

(Continued)

*Primary Examiner* — Benjamin J Packard
(74) *Attorney, Agent, or Firm* — Merchant & Gould P.C.

(57) ABSTRACT

A conjunctival cover including an annular generally curved shell having a conjunctival portion structured to conform to and overly at least part of the conjunctiva of an eye. The annular generally partially spherical shell defines a generally central opening. The central opening is sized to leave a cornea of the eye substantially or partially uncovered when the conjunctival cover is applied to the eye.

12 Claims, 7 Drawing Sheets

(56) References Cited

U.S. PATENT DOCUMENTS

| | | |
|---|---|---|
| 4,194,815 A | 3/1980 | Trombley |
| 4,201,210 A | 5/1980 | Hughes |
| 4,235,985 A | 11/1980 | Tanaka et al. |
| 4,353,849 A | 10/1982 | Lewison |
| 4,464,026 A | 8/1984 | Comparetto |
| 4,652,099 A | 3/1987 | Lichtman |
| 4,744,647 A | 5/1988 | Meshel et al. |
| 4,886,350 A | 12/1989 | Wichterle |
| 5,114,686 A | 5/1992 | Gillespie |
| 5,245,367 A | 9/1993 | Miller et al. |
| 5,396,583 A | 3/1995 | Chen et al. |
| 5,580,498 A | 12/1996 | Sugiyama et al. |
| 5,658,602 A | 8/1997 | Martin et al. |
| 5,757,458 A | 5/1998 | Miller et al. |
| 5,804,107 A | 9/1998 | Martin et al. |
| 5,929,968 A | 7/1999 | Cotie et al. |
| 5,953,098 A | 9/1999 | Lieberman et al. |
| 5,980,040 A | 11/1999 | Xu et al. |
| 6,039,899 A | 3/2000 | Martin et al. |
| 6,312,393 B1 | 11/2001 | Abreu |
| 6,794,456 B2 | 9/2004 | Grobe, III |
| 6,880,932 B2 | 4/2005 | Doshi |
| 7,249,849 B2 | 7/2007 | Marmo et al. |
| 7,559,649 B2 | 7/2009 | Cotie et al. |
| 7,691,916 B2 | 4/2010 | McCabe et al. |
| 7,695,135 B1 | 4/2010 | Rosenthal |
| 7,699,464 B2 | 4/2010 | Iuliano |
| 7,864,440 B2 | 1/2011 | Berge |
| 8,118,426 B2 | 2/2012 | Cotie et al. |
| 8,149,512 B2 | 4/2012 | Kim |
| 8,184,068 B1 | 5/2012 | Rhodes |
| 8,184,069 B1 | 5/2012 | Rhodes |
| 8,216,306 B2 | 7/2012 | Coroneo |
| 8,228,315 B1 | 7/2012 | Starner |
| 8,450,387 B2 | 5/2013 | McCabe et al. |
| 8,459,793 B2 | 6/2013 | de Juan, Jr. et al. |
| 8,471,783 B2 | 6/2013 | Rhodes |
| 8,480,227 B2 | 7/2013 | Qiu et al. |
| 8,482,487 B1 | 7/2013 | Rhodes |
| 8,506,944 B2 | 8/2013 | Sullivan et al. |
| 8,599,490 B2 | 12/2013 | Lee |
| 8,736,692 B1 | 5/2014 | Wong |
| 8,742,623 B1 | 6/2014 | Biederman et al. |
| 8,764,185 B1 | 7/2014 | Biederman et al. |
| 8,827,447 B2 | 9/2014 | Awasthi et al. |
| 8,864,306 B2 | 10/2014 | de Juan, Jr. et al. |
| 8,867,141 B2 | 10/2014 | Pugh |
| 8,895,763 B2 | 11/2014 | Reif |
| 8,911,083 B2 | 12/2014 | Brent |
| 8,985,763 B1 | 3/2015 | Etzkorn et al. |
| 9,046,699 B2 | 6/2015 | Caldarise |
| 9,198,752 B2 | 12/2015 | Woods |
| 9,310,627 B2 | 4/2016 | Havenstrite et al. |
| 9,395,557 B2 | 7/2016 | Thompson |
| 9,551,885 B2 | 1/2017 | Sindt et al. |
| 9,668,916 B2 | 6/2017 | Thompson |
| 9,869,883 B2 | 1/2018 | Thompson |
| 9,910,295 B2 | 3/2018 | Thompson |
| 10,353,220 B2 | 7/2019 | Thompson |
| 10,449,086 B2 | 10/2019 | Thompson |
| 10,548,767 B2 | 2/2020 | Thompson |
| 10,678,067 B2 | 6/2020 | Thompson |
| 10,684,493 B2 | 6/2020 | Thompson |
| 10,959,834 B2 | 3/2021 | Thompson |
| 11,076,985 B2 | 8/2021 | Thompson |
| 2002/0063848 A1 | 5/2002 | Fiala |
| 2003/0105521 A1 | 6/2003 | Perez |
| 2003/0125498 A1 | 7/2003 | McCabe et al. |
| 2003/0162862 A1 | 8/2003 | McCabe et al. |
| 2004/0096477 A1 | 5/2004 | Chauhan et al. |
| 2005/0046794 A1 | 3/2005 | Silvestrini |
| 2006/0007391 A1 | 1/2006 | McCabe et al. |
| 2006/0132707 A1 | 6/2006 | Tung |
| 2007/0016292 A1 | 1/2007 | Perez |
| 2007/0225691 A1 | 9/2007 | Silvestrini et al. |
| 2007/0229757 A1 | 10/2007 | McCabe et al. |
| 2007/0242216 A1 | 10/2007 | Dootjes |
| 2007/0298220 A1 | 12/2007 | Noda |
| 2008/0002149 A1 | 1/2008 | Fritsch |
| 2008/0015282 A1 | 1/2008 | McCabe et al. |
| 2008/0024717 A1 | 1/2008 | Kim |
| 2008/0182956 A1 | 7/2008 | Stanbro et al. |
| 2008/0243095 A1 | 10/2008 | Kaiser |
| 2008/0316424 A1 | 12/2008 | McCabe et al. |
| 2010/0072642 A1 | 3/2010 | Broad et al. |
| 2010/0084775 A1 | 4/2010 | McCabe et al. |
| 2010/0092452 A1 | 4/2010 | Sullivan et al. |
| 2010/0133710 A1 | 6/2010 | McCabe et al. |
| 2010/0232031 A1 | 9/2010 | Batchko |
| 2010/0233241 A1 | 9/2010 | Leahy et al. |
| 2011/0059902 A1 | 3/2011 | Sullivan et al. |
| 2011/0070222 A1 | 3/2011 | Sullivan et al. |
| 2011/0116034 A1 | 5/2011 | Goto et al. |
| 2011/0142908 A1 | 6/2011 | Sullivan et al. |
| 2011/0146206 A1 | 6/2011 | Stanbro et al. |
| 2011/0184358 A1 | 7/2011 | Weiner |
| 2011/0273663 A1 | 11/2011 | Pugh |
| 2011/0282328 A1 | 11/2011 | Ambati et al. |
| 2012/0193822 A1 | 8/2012 | McCabe et al. |
| 2012/0245444 A1 | 9/2012 | Otis et al. |
| 2012/0268711 A1 | 10/2012 | Lai |
| 2012/0321611 A1 | 12/2012 | Sullivan et al. |
| 2013/0053953 A1 | 2/2013 | Silvestrini |
| 2013/0077044 A1 | 3/2013 | de Juan, Jr. et al. |
| 2013/0225715 A1 | 8/2013 | McCabe et al. |
| 2013/0237631 A1 | 9/2013 | McCabe et al. |
| 2013/0261569 A1 | 10/2013 | Weiner et al. |
| 2013/0265507 A1 | 10/2013 | Ford et al. |
| 2013/0278890 A1 | 10/2013 | de Juan, Jr. et al. |
| 2014/0192315 A1 | 7/2014 | Liu et al. |
| 2014/0192327 A1 | 7/2014 | Sindt et al. |
| 2014/0377327 A1 | 12/2014 | Davis et al. |
| 2015/0041736 A1 | 2/2015 | McCabe et al. |
| 2015/0092156 A1 | 4/2015 | Qiu et al. |
| 2015/0157315 A1 | 6/2015 | Theobald |
| 2015/0305929 A1 | 10/2015 | Goldberg et al. |
| 2015/0366708 A1 | 12/2015 | Lerner |
| 2016/0054589 A1 | 2/2016 | Otts et al. |
| 2016/0056508 A1 | 2/2016 | Flitsch et al. |
| 2016/0067035 A1 | 3/2016 | Gontijo |
| 2016/0223836 A1 | 8/2016 | Havenstrite et al. |
| 2016/0266405 A1 | 9/2016 | Thompson |
| 2017/0082869 A1 | 3/2017 | Sindt et al. |
| 2017/0087014 A1 | 3/2017 | Potter, Jr. et al. |
| 2017/0160432 A1 | 6/2017 | Havenstrite et al. |
| 2017/0242271 A1 | 8/2017 | Pugh et al. |
| 2017/0329053 A1 | 11/2017 | Wang et al. |
| 2018/0001581 A1 | 1/2018 | Patel et al. |
| 2018/0107024 A1 | 4/2018 | Thompson |
| 2018/0120589 A1 | 5/2018 | Thompson |
| 2019/0310493 A1 | 10/2019 | Thompson |
| 2020/0004046 A1 | 1/2020 | Thompson et al. |
| 2020/0085564 A1 | 3/2020 | Thompson |
| 2020/0085565 A1 | 3/2020 | Thompson |
| 2020/0237555 A1 | 7/2020 | Thompson |
| 2020/0301169 A1 | 9/2020 | Thompson |
| 2020/0310160 A1 | 10/2020 | Thompson |
| 2022/0031505 A1 | 2/2022 | Thompson |
| 2022/0117723 A1 | 4/2022 | Thompson |
| 2022/0308363 A1 | 9/2022 | Thompson |
| 2023/0221580 A1 | 7/2023 | Thompson |

FOREIGN PATENT DOCUMENTS

| | | |
|---|---|---|
| EP | 1629317 A2 | 3/2006 |
| EP | 2276496 A1 | 1/2011 |
| EP | 2276497 A1 | 1/2011 |
| EP | 2632532 A2 | 9/2013 |
| FR | 2740232 | 4/1997 |
| JP | 2951334 | 7/1999 |
| KR | 20050052442 A | 6/2005 |
| KR | 2020140003482 | 6/2014 |
| WO | WO1995008135 | 3/1995 |
| WO | WO1997034185 | 9/1997 |

(56) References Cited

FOREIGN PATENT DOCUMENTS

| | | |
|---|---|---|
| WO | WO2001033284 | 5/2001 |
| WO | WO2002006883 | 1/2002 |
| WO | WO2003022321 | 3/2003 |
| WO | WO2004109368 | 12/2004 |
| WO | WO2005034730 | 4/2005 |
| WO | WO2005121874 | 12/2005 |
| WO | WO2007008666 | 1/2007 |
| WO | WO2009069264 | 6/2009 |
| WO | WO2009137602 | 11/2009 |
| WO | WO2009137603 | 11/2009 |
| WO | WO2010105130 | 9/2010 |
| WO | WO2011050287 | 4/2011 |
| WO | WO2012051223 | 4/2012 |
| WO | WO2012058382 | 5/2012 |
| WO | WO2014012016 | 1/2014 |
| WO | WO2014074477 | 5/2014 |
| WO | WO2014100836 | 6/2014 |
| WO | WO2014205252 | 12/2014 |
| WO | WO2015073758 | 5/2015 |
| WO | WO2016014403 | 1/2016 |
| WO | WO2016090863 | 6/2016 |
| WO | WO2016115369 | 7/2016 |
| WO | WO 2016/144483 | 9/2016 |
| WO | WO2016145204 | 9/2016 |
| WO | WO2017037611 | 3/2017 |
| WO | WO2017053673 | 3/2017 |
| WO | WO2017096087 | 6/2017 |
| WO | WO2017103793 | 6/2017 |

OTHER PUBLICATIONS

Application and File History for U.S. Appl. No. 14/071,240, filed Nov. 4, 2013. Inventor: Vance M. Thompson.
Application and File History for U.S. Appl. No. 15/608,503, filed May 30, 2017. Inventor: Vance M. Thompson.
Application and File History for U.S. Appl. No. 15/827,582, filed Nov. 30, 2017. Inventor: Vance M. Thompson.
Ciolino et al., "In vivo performance of a drug-eluting contact lens to treat glaucoma for a month", Biomaterials, 35 (2014), 432-439.
Innovative drug-dispensing contact lens delivers glaucoma mediation continuously for a month, Ophthalmology, Dec. 9, 2013, 2 pages.
PCT International Preliminary Report on Patentability for International Application No. PCT/US2014/063696 dated May 10, 2016.
PCT International Search Report for International Application No. PCT/US2014/063696, dated Feb. 12, 2015.
PCT Written Opinion for International Application No. PCT/US2014/063696, dated Feb. 12, 2015.
Piggyback Lens for Advanced Keratoconus, prior to Dec. 6, 2013, pp. 18-19.
Ren et al., "Adaptive Liquid Lens by Changing Aperture," Journal of Microelectromechanical Systems, vol. 21, No. 4, pp. 953-958, Aug. 2012.
Severinsky et al., "Current applications and efficacy of sclera contact lenses—a retrospective study", J Optom. 2010;3(3):158-163.
STIC Search, 50 pages, Oct. 28, 2016.

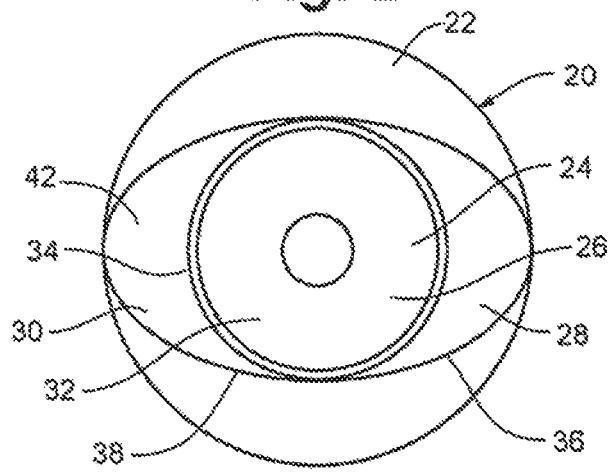
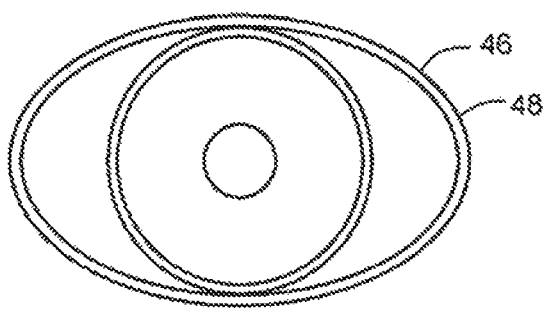
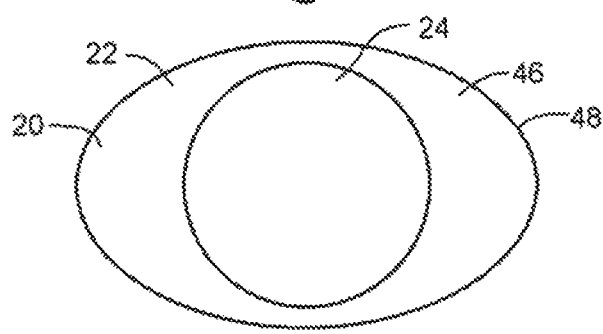

CONJUNCTIVAL COVER AND METHODS THEREFOR

CROSS-REFERENCE TO RELATED APPLICATIONS

This application is a continuation of U.S. patent application Ser. No. 17/376,686, filed Jul. 15, 2021, now U.S. Pat. No. 11,672,698, which is a continuation of U.S. patent application Ser. No. 16/777,358, now U.S. Pat. No. 11,076,985, filed Jan. 30, 2020, which is a continuation of U.S. patent application Ser. No. 15/827,582, now U.S. Pat. No. 10,548,767, filed Nov. 30, 2017, which is a continuation of U.S. patent application Ser. No. 15/608,503, now U.S. Pat. No. 10,449,086, filed May 30, 2017, which is a continuation of U.S. patent application Ser. No. 14/071,240, now U.S. Pat. No. 9,668,916, filed Nov. 4, 2013, each of which is hereby fully incorporated herein by reference.

TECHNICAL FIELD

The invention relates generally to the field of treatment of dry eye syndrome and to the field of medication delivery by inserts.

BACKGROUND

Contact lenses have been in existence for many decades. Early contact lenses were made of glass or rigid plastic such as polymethylmethacrylate. Early contact lens designs were quite large and referred to as scleral or haptic lens. Scleral or haptic contact lens designs cover the cornea completely as well as covering a large portion of the conjunctiva or sclera of the eye. The sclera is the structural white of the eyeball while the conjunctiva is a transparent tissue which overlies the sclera as well as covering the backside of the eye lids. Early contact lens designs were made of rigid, largely oxygen impermeable polymers as discussed above or a very few of glass. Because corneal physiology was poorly understood at the time these lenses were made, they often cause great discomfort and negative effect on the corneal health.

As time went by, in the 1950's, hard contact lenses made of polymethylmethacrylate became much smaller having a diameter significantly smaller than that of the cornea. Hard corneal contact lenses were more comfortable and less physiological damaging than scleral or haptic lenses, but only marginally so. Hard contact lenses still significantly deprived the cornea of a necessary oxygen supply from atmospheric oxygen to maintain good corneal health and were difficult to adapt to. In the 1970s, so called soft corneal contact lenses became available. Soft contact lenses generally were larger than hard corneal contact lenses having a diameter approximating that of the cornea, somewhat larger than the cornea or somewhat smaller than the cornea. Soft contact lenses are generally made of hydrophilic polymers that absorb substantial amounts of water, saline solution or the tear film. Soft contact lenses also provided improved comfort due to their permeability to oxygen and due to their more flexible nature. Later still, so called gas-permeable contact lenses became available. Gas permeable rigid contact lenses are similar in size and structure to hard corneal contact lenses but are made of rigid oxygen permeable polymers that allow oxygen and other gases to pass through the material of the contact lens to provide improved corneal health. Generally, rigid contact lenses provide sharper vision than soft contact lenses though this is not universally true.

Hard contact lenses are well as scleral or haptic contact lenses were sometimes fenestrated. That is, tiny holes were drilled or otherwise formed through the rigid contact lens material in an effort to improve tear exchange under the contact lens or to provide a greater availability of oxygen through the contact lens. Fenestration was generally not a very successful technique. Fenestrations, however, were uniformly tiny holes generally much smaller than one millimeter in diameter, occasionally multiple fenestrations were present.

All contact lenses known to the applicants provide substantially or complete coverage of the cornea of the eye.

Drug delivery inserts are also known to exist. Drug delivery inserts are small containers into which drugs or pharmaceuticals are placed or absorbed that exist in several different forms. Subpalpebral drug delivery inserts are generally intended to be inserted behind the eye lid in the conjunctival fornices and to gradually release a desired medication to provide a slow, continuous supply of drug to the eye. Subpalpebral drug delivery inserts generally have suffered from being uncomfortable for the patient to tolerate and subject to be accidentally dislodged from the eye by rubbing of the eye or other movements. In addition, subpalpebral drug delivery inserts sometimes cause irritation of the conjunctiva or the eye lids.

Another variety of drug delivery insert is intended to be surgically inserted within the globe of the eye to gradually leach out a steady supply of a desired drug into the intraocular environment. Intraocular drug delivery inserts are less often used due to their relatively invasive nature.

Generally, drug delivery inserts whether subpalpebral or intraocular have contained a single drug.

Dry eye syndrome is one of the most commonly treated eye problems in the United States. Dry eye syndrome is also known as keratitis sicca, keratoconjunctivitis sicca (KCS) xerophthalmia, and lacrimal insufficiency. It is estimated that over ten million Americans and 30 million persons worldwide suffer from dry eye syndrome.

For a large fraction of dry eye patients, dry eye syndrome creates discomfort or annoyance. For those severely afflicted, dry eye syndrome can be debilitating and, in some circumstances, even sight-threatening. In extremely severe cases, dry eye syndrome can even lead to the loss of an eye.

Dry eye syndrome typically results from deficiency in the quality or quantity of tears produced by the patient. Precorneal tear film has traditionally been considered to have a three-layered structure. The closest to the cornea lies the mucin, or mucus, layer. The mucin layer provides an interface between the corneal epithelium and the remainder of the tear film. Overlying the mucin layer is the watery aqueous layer, which is the thickest layer of the three. The outermost layer of the precorneal tear film is the lipid layer. The lipid layer is an oily film that reduces evaporation from the aqueous layer beneath it.

The middle aqueous layer provides moisture to the corneal tissue, carries important nutrients, and serves to remove metabolic waste produced by the cornea. Deficiency in any of the three layers of the precorneal tear film can result in complaints of dry, gritty feeling or burning eyes.

The mucin that forms the mucin layer, nearest the cornea, is secreted by goblet cells in the conjunctiva. The conjunctiva is the transparent tissue that covers the sclera and the backside of the eyelids. The mucin layer functions to decrease surface tension of the tear film. In addition, the cornea itself is hydrophobic. Without the mucin layer to provide a bridge between the cornea and the aqueous layer, the aqueous layer would bead up and allow dry spot formation on the cornea.

The aqueous layer is secreted primarily by the glands of Wolfring and Krause located in the eyelid margin. The aqueous layer helps provide an optically smooth, transparent surface to the precorneal tear film. The lipid layer is secreted by the meibomian glands, and the glands of Zeiss and Moll. The glands of Zeiss and Moll are also located at the eyelid margin.

Blinking is essential to maintenance of the precorneal tear film. During each blink, the eyelid wipes over the surface of the cornea, smoothing the mucin layer and spreading the overlying aqueous and lipid layers to provide a completely wetted surface. In between blinks, the tear film thins due to evaporation of the aqueous layer. If evaporation is excessive, dry spots may form on the surface of the cornea.

Deficiency, or imperfect quality, of any of the three component layers can lead to dry eye symptoms. Many systemic and external factors can contribute to dry eye syndrome. For example, Sjogren's syndrome is associated with arthritic diseases in combination with dry eye and dry mouth. Deficiency of Vitamin A, use of oral contraceptives and environmental factors can all contribute to dry eye syndrome.

Recent research into the natural history of dry eye syndrome has shown that the disease progresses through four stages. Each stage is a consequence of the preceding stage. The stages are:
1. Loss of water from the aqueous layer of the tear film leading to an increase in the tear film osmolarity;
2. Loss of conjunctival goblet cells and decreased corneal glycogen;
3. Increased loss of corneal squamous epithelial cells;
4. Destabilization of the interface between the corneal surface and the tear film.

Either decreased secretion of tear film components or increased evaporation lead to increased tear film osmolarity and the following stages that lead to eventual corneal decompensation and the serious consequences of dry eye syndrome.

The adnexa of the eye may also be involved in dry eye syndrome. The adnexa of the eye include the structures surrounding the eye such as the eyelids, eye lashes, the tear drainage and tear production structures. Blepharitis commonly contributes to dry eye syndrome. Blepharitis typically results from bacterial infection of the tiny glands in the margin of the eyelid. These glands include the glands of Zeiss, Moll and Wolfring as well as the meibomian glands. Most commonly, the affected glands are the meibomian glands. In bacterial blepharitis, bacterial infection causes the meibomian glands to become plugged, and thus not be able to produce a normal lipid layer to contribute to the tear film. Some bacteria that infect the glands also secrete exotoxins that seep out of the glands into the eye and injure the corneal epithelium.

Treatments of dry eye syndrome vary depending upon the type of presentation. The most common treatment for dry eye syndrome is the use of artificial tear supplements to provide additional moisture and lubrication to the corneal surface. Artificial tear eye drops are placed on the eye by the patient. Artificial tear supplements must be used regularly and often to be effective.

Lubricant ointments may also be employed. Ointments are usually used at bedtime because they tend to be messy and blur vision. For some patients, even the use of ointments is not sufficient to provide comfort during sleep.

Tears drain from the eye through the lacrimal drainage system. Tiny openings at the nasal corner of each upper and lower eyelid are called the lacrimal puncta. The lacrimal puncta lead into ducts that drain into the nasopharynx.

One treatment for dry eye syndrome is to partially or completely close one or more lacrimal puncta to reduce tear outflow into the lacrimal drainage apparatus. Traditionally, this closure was accomplished surgically or by cautery. In the last decade, however, temporary and permanent punctal occlusion plugs have been utilized.

Permanent punctal plugs are typically made from surgical silicone; temporary plugs are generally made of soluble collagen. Collagen plugs dissolve over a period of days and are helpful in diagnosis.

Punctal plugs are placed into the lacrimal puncta, or lacrimal drainage ducts. The plugs impede the outflow of tears from the eye. This approach slows the outflow of tears and retains them in the eyes longer, often relieving symptoms. Punctal plugs have the distinct advantage of being readily removable and avoid the issues of scar formation.

Blepharitis is sometimes treated by the use of antibiotic medications. Another important treatment for blepharitis is the application of warm soaks and lid scrubs. In this form of treatment, the patient applies a warm wet washcloth to the eyelids for a period of time to provide humidity, warmth and to help soften blockage of and restore flow from the meibomian glands. Lid scrubs are practiced by taking a mild, nonirritating soap and vigorously scrubbing the eyelid margins with the eyes closed, so as to massage the meibomian glands and increase production. The surfactant helps to dissolve the greasy blockage of the meibomian glands.

Patients who have severe dry eye syndrome often suffer disrupted sleep because they cannot go for longer than an hour or so without applying tear supplements to the eyes. This can lead to pronounced sleep deprivation and a consequent reduction in quality of life.

A variety of researchers have been seeking other medicinal treatments for dry eye syndrome. Largely, this research is directed at pharmaceutical efforts to increase tear production.

Despite the many treatment options available, there remains no cure for dry eye syndrome. A great many patients still have substantial and even debilitating discomfort because of dry eye syndrome. Very few treatment options exist to provide comfort for dry eye syndrome patients during sleep.

Accordingly, there is still room for improvement in the arts of treating dry eye syndrome and in the art of drug delivery inserts.

SUMMARY

According to one embodiment of the invention, many of the above discussed problems are solved by an annular conjunctival cover. In the context of the invention, annular does not necessarily limit the invention to a circular structure with an opening in the center. The invention is annular in the sense that it covers the conjunctiva surrounding the cornea while leaving the cornea completely or substantially uncovered. The conjunctival cover make take other shapes as described and depicted herein while still being "annular" in the sense of the invention. According to one embodiment of the invention, the cornea is left completely uncovered and exposed. According to another embodiment of the invention, at least 80% of the corneal diameter is left uncovered and exposed. According to another embodiment of the invention, at least 50% of the corneal diameter is left uncovered and exposed.

Accordingly, the annular conjunctival cover generally covers the conjunctiva partially or completely but does not the cornea completely. According to an embodiment of the invention, the cornea is not covered by the annular conjunctival shield centrally. The cornea may have some coverage in the peripheral portions.

According to one embodiment of the invention, the conjunctival cover retains mucin and aqueous tear components under the cover. In this embodiment, the conjunctival cover provides a reservoir of tears so that with blinking the reservoir of tears, or mucin and aqueous tear components is flushed out from under the conjunctival cover and is directed to the cornea to assist in promoting corneal health.

According to another embodiment of the invention, evaporation of tears from the conjunctival surface is reduced.

According to another embodiment of the invention, the cornea is partially covered to allow shaping of the anterior corneal tear film over the central cornea in such a way as to be corrective for vision. According to this embodiment of the invention, a tear film lens would be created though not in the sense of a tear lens that is created between a rigid contact lens and the cornea but in the sense that an alteration of the curvature of the tear film overlying the central uncovered cornea is altered to provide some vision correction. The conjunctival cover may or may not have optical power of its own but structure surrounding the central opening may be varied to create a tear lens in the central opening that may contribute to correction of myopia, hyperopia, astigmatism or presbyopia. The tear lens of the central opening may also provide a prismatic correction based on structure surrounding the central opening.

According to one embodiment of the invention, the curvature of the annular conjunctival cover is flatter than that of the conjunctival surface. According to another embodiment of the invention, the curvature of the annular conjunctival cover approximately parallels the conjunctival surface. According to yet another embodiment of the invention, the annular conjunctival cover is steeper in curvature than the covered conjunctival surface.

According to another embodiment of the invention, the annular conjunctival cover has an overall diameter approximating that of the palpebral fissure so that an outer edge of the annular conjunctival cover extends substantially into the fornices superiorly and inferiorly. According to another embodiment of the invention, the annular conjunctival cover has a diameter significantly less than the diameter required to extend to the fornices. According to another embodiment of the invention, the annular conjunctival cover is not circular but instead has a spindle or football shaped so as to cover the otherwise exposed nasal and lateral conjunctiva more completely than the superior and inferior conjunctiva. In this case, the annular conjunctival cover may optionally include a prism ballast wherein the lower portion of the annular conjunctival cover is thicker than the upper portion or other ballast to encourage desired positioning.

The annular conjunctival cover, according to another example embodiment of the invention, is formed from materials similar to those used to make soft contact lenses. For example, the annular conjunctival cover may be formed of collagen, hydrophilic polymers or non-hydrophilic polymers of a flexible nature. The annular conjunctival cover may be formed in a single layer or may include multiple layers.

The annular conjunctival cover according to another example embodiment of the invention may include a drug delivery function. For example, the annular conjunctival cover may include one or more physical reservoirs into which a drug desired to be delivered to the eye is placed. According to another example embodiment, a drug to be administered in an aqueous solution or suspension may be absorbed into hydrophilic material of the annular conjunctival cover. Other non aqueous or partially aqueous vehicles may also be used. According to yet another embodiment of the invention, multiple drug reservoirs may be present so that multiple drugs may be delivered to the eye simultaneously from different individual reservoirs without the mixing of the drugs into a single delivery medium.

When the annular conjunctival shield is utilized as a drug delivery mechanism, drugs delivered may include antibiotics, steroids, anti-glaucoma medications, anti-viral medications, anti-viral medications, NSAIDS, ocular surface lubricants and other drugs useful in treating dry eye including cyclosporine to inhibit the inflammatory response.

Further drugs or active agents that can be delivered by drug delivery conjunctival cover include, for example, but are not limited to: Anti-infectives: such as antibiotics, including tetracycline, chlortetracycline, bacitracin, neomycin, polymyxin B, gramicidin, oxytetracycline, chloramphenicol, and erythromycin; sulfonamides, including sulfacetamide, sulfamethizole, sulfisoxazole; quinolones, including ofloxacin, norfloxacin, ciprofloxacin, sporfloxacin; aminoglycosides, including amikacin, tobramycin, gentamicin; cephalosporins; combinations of antibiotics; antivirals, including idoxuridine, trifluridine, vidarabine cidofovir, foscarnet sodium, ganciclovir sodium and acyclovir; antifungals such as amphotericin B, nystatin, flucytosine, fluconazole, natamycin, miconazole and ketoconazole; and other anti-infectives including nitrofurazone and sodium propionate.

Anti-allergy medications such as antzoline, methapyriline, chlorpheniramine, pyrilamine and prophenpyridamine, emedastine, ketorolac, levocabastin, lodoxamide, lotepredonol, naphazoline/antazoline, naphazoline/pheniramine, olopatadine and cromolyn sodium. Anti-inflammatories: such as hydrocortisone, hydrocortisone acetate, dexamethasone, dexamethasone 21-phosphate, fluocinolone, medrysone, prednisolone, prednisolone 21-phosphate, prednisolone acetate, fluorometholone, fluorometholone acetate, meddrysone, loteprednol etabonate, rimexolone. Nonsteroidal anti-inflammatories: such as flurbiprofen, suprofen, diclofenac, indomethacin, ketoprofen, and ketorolac. Decongestants: such as phenylephrine, naphazoline, oxymetazoline, and tetrahydrazoline. Miotics and anticholinesterases: such as pilocarpine, eserine talicylate, carbachol, diisopropyl fluorophosphate, phospholine iodide, and demecarium bromide.

Mydriatics: such as atropine sulfate, cyclopentolate; homatropine, scopolamine, tropicamide, eucatropine, and hydroxyamphetamine.

Other medications include but are not limited to antiglaucoma agents: such as adrenergics, including epinephrine and dipivefrin, epinephryl borate; .beta.-adrenergic blocking agents, including levobunolol, betaxolol, metipranolol, timolol, carteolol; alpha.-adrenergic agonists, including apraclonidine, clonidine, brimonidine; parasympathomimetics, including pilocarpine, carbachol; cholinesterase inhibitors, including isoflurophate, demecarium bromide, echothiephate iodide; carbonic anhydrase inhibitors, including dichlorophenamide acetazolamide, methazolamide, dorzolamide, brinzolamide, dichlorphenamide; prostaglandins, including latanoprost, travatan, bimatoprost; diconosoids and combinations of the above, such as a .beta.-adrenergic blocking agent with a carbonic anhydrase inhibitor.

Anticataract drugs: such as aldose reductase inhibitors including tolerestat, statol, sorbinil; antioxidants, including ascorbic acid, vitamin E; nutritional supplements, including glutathione and zinc.

Lubricants: such as glycerin, propylene glycol, polyethylene glycol and polyglycerins may also be delivered. Omega 3 fatty acids and vitamin supplements may also be delivered.

The annular conjunctival cover may be used to deliver any drug that would otherwise be delivered in an eye drop or ointment or by injection or other routes of administration.

The annular conjunctival cover can release drugs through diffusion out of it if the drug is absorbed therein or by gradual dissolving of the walls of the drug reservoirs. Drugs can be released at different time periods by structuring the drug reservoirs for differential times of dissolution such as by variable wall thickness. Drugs may also be released through active pumping from blinking or through stronger active pumping through active eye squeezing by the patient.

In addition, the annular conjunctival cover may be made of materials that are bioabsorbable or non-absorbable. Similar to contact lenses, the annular conjunctival cover may be designed for short term or extended use. For example, the device may be designed for single day use, weekly use, monthly use, six month use, one year use or longer.

According to another embodiment of the invention, the annular conjunctival cover may be intrapalpebral in nature in that it covers the conjunctiva where it is normally exposed with the eye open between the eyelid margins. According to another embodiment of the invention, mucous and aqueous components of the tear film that form the natural lubricants of the eye are present on the conjunctiva and thus susceptible to evaporation into the environment. For an individual with normal adequate tear production this is generally not a problem. For a dry eye patient controlling tear evaporation may make a large difference in comfort and ocular anterior segment health. According to one embodiment of the invention, the tear film may be contained or preserved between the annular conjunctival cover as well as being present overlying the annular conjunctival cover. Thus, the tear film would be divided into two residence locations, one between the device and the conjunctiva and another on top of the annular conjunctival cover. This dual reservoir of tear film is expected to be directed onto the cornea at the time of a blink, the overlying tear film by the normal blinking mechanism and the underlying tear film by the squeezing or pressing of the annular conjunctival cover against the conjunctiva by the action of the eyelids. Further tear reservoirs can be provided by forming the conjunctival cover to have multiple layers that may define multiple tear reservoirs. Normal or intentional eye movements are expected to also contribute to distribution of tears from two or more tear reservoirs to the corneal surface. For example, if a blink does not expel a majority of tear contents held under the lower lid the patient might learn to look upward and the straight ahead to such that the lower eyelid margin presses or squeezes the tears onto the cornea in the manner of a squeegee. The same may be found true for medications in drug reservoirs. A blink may express a certain amount but purposeful upward or downward gaze may be found to squeeze out further tears or medication onto the corneal surface. Forcefully closing the eyes may be another way to expel contents that reside in or under the conjunctival cover or in the drug reservoirs because of the squeezing effect of the eye lids against the globe. Patients may be directed to do so to expel more contents on demand. Digital massage over the upper or lower eyelid may be utilized to expel tear contents or the contents of drug reservoirs.

The conjunctival cover may also be used for sampling purposes. The conjunctival cover may be placed on the eye to absorb tears or other desired substances that may then be recovered for laboratory testing for, for example, but not limited to diagnostic testing for dry eye tests, sugar content, or other tests.

According to one example embodiment of the invention, the annular conjunctival cover is a single use disposable product. According to another embodiment of the invention, the annular conjunctival cover is structured for multiple uses with associated cleaning and disinfection as needed and desired.

According to another embodiment of the invention, the conjunctival cover may incorporate an intraocular pressure monitor or other monitor that monitors one or more ocular functions. For example, the conjunctival cover may incorporate a strain gauge or intraocular pressure monitor similar to that of the Sensimed Triggerfish by Sensimed of Switzerland.

According to another example embodiment of the invention, the conjunctival cover may incorporate transparent or opaque tinting or portions. This can be utilized to, for example, obscure unsightly scars or pigmentation of the conjunctiva as well as for cosmetic purposes. Tinting may be used to change the color of the conjunctiva for fun or may include an onlay, inlay or temporary tattoo.

According to another embodiment of the invention, the invention includes a method in which a physician or other health professional places the annular conjunctival cover on the eye where it remains until being removed by the physician. Alternately, a patient may place and remove the annular conjunctival cover on the eye thus providing an opportunity to rehydrate or reload the annular conjunctival cover with a lubricant or a drug medication to be delivered, thus, relieving the patient of the necessity to use eye drops several times during the day or for whatever other period of time that drops are generally used or, at least reducing the frequency at which eye drop application is required. This also provides for a continuous supply of medication being delivered on a continuous basis.

According to another example embodiment, medication is housed within the annular conjunctival cover in multiple individual reservoirs that are formed of an absorbable material that degrades over time.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIG. 2 is a schematic depiction of an annular conjunctival cover applied to an eye according to an example embodiment of the invention;

FIG. 3 is a is a schematic depiction of an elliptical annular conjunctival cover applied to an eye according to an example embodiment of the invention;

FIG. 4 is a schematic depiction of an elliptical annular conjunctival cover isolated from the eye according to an example embodiment of the invention;

Figure 1:
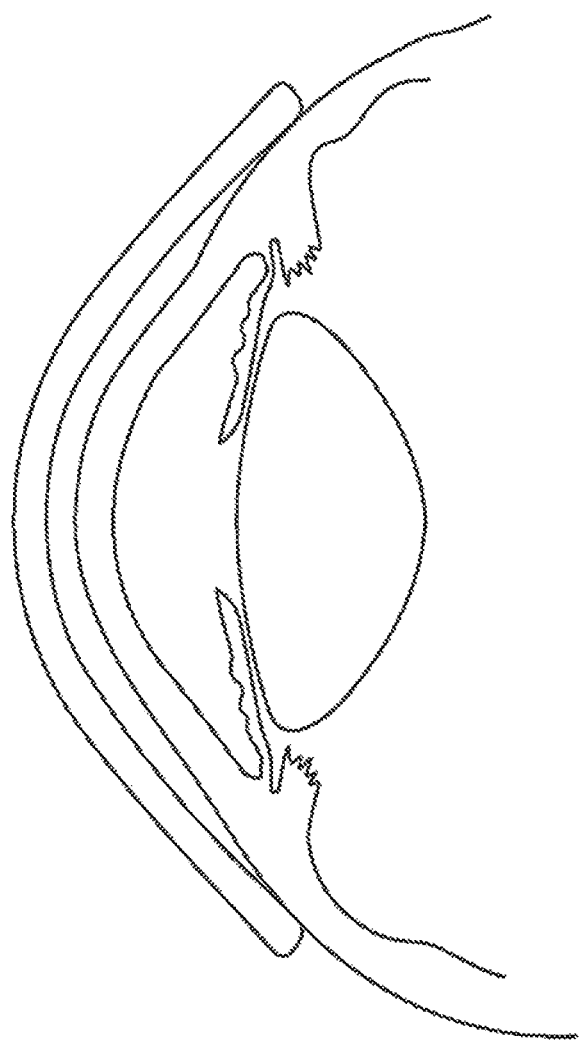
FIG. 1 is a schematic depiction of a prior art scleral contact lens.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Referring generally to FIGS. 1-10, conjunctival cover 20 according to an embodiment of the invention, generally includes annular shell 22 presenting central opening 24. Annular shell 22 is formed of a hydrophilic or non-hydrophilic flexible material similar to those used in the manufacture and construction of soft contact lenses. Conjunctival cover 20 is utilized in relation to an eye 26. Eye 26 generally includes sclera 28, conjunctiva 30, cornea 32, limbus 34 and eyelids 36. The sclera is the structural white portion of the eye that forms the majority of the eyeball. Conjunctiva 30 overlies the sclera and includes palpebral conjunctiva 40 and bulbar conjunctiva 42. Palpebral conjuctiva 40 and bulbar conjuctiva 42 meet at fornices 44. Cornea 32 is the clear front part of the eye and is generally dome shaped in structure. Limbus 34 is the juncture between the edge of the cornea 32 and sclera 28. Conjunctival cover 20 generally covers bulbar conjuctiva 42 while leaving all or a portion of cornea 32 exposed. For this purpose, central opening 24 is positioned to generally coincide with cornea 32. Annular shell 22 of conjunctival cover 20 may be sized to extend into fornices 44 or may be smaller in size.

Referring to FIGS. 3 and 4, another embodiment of conjunctival cover 20 is elliptical conjunctival cover 46. Elliptical conjunctival cover 46 includes annular shell 22 having generally elliptical peripheral margin 48. Elliptical conjunctival cover 46 may be sized so that elliptical peripheral margin 48 is generally coincident with eyelid margins 38. Accordingly, elliptical peripheral margin 48 may extend partially under eyelid margins 38 or may be slightly smaller than the space bounded by eyelid margins 38 when eye 26 is open.

Figure 5:
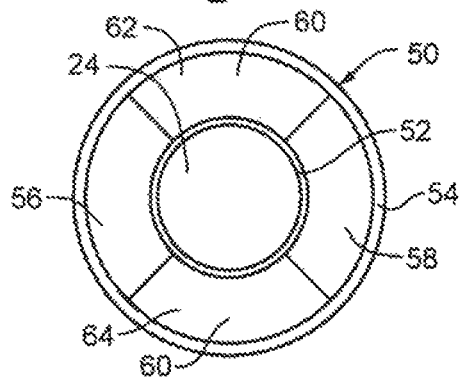
FIG. 5 is a schematic depiction of a conjunctival cover having an inner ring, an outer ring and a segmented structure according to an example embodiment of the invention.
Figure 6:
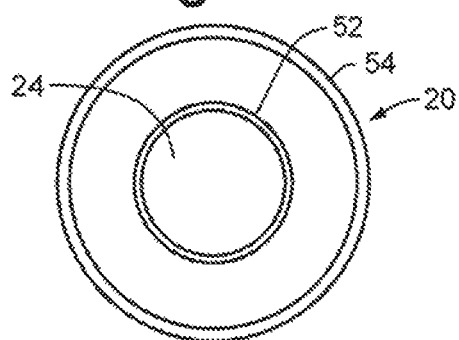
FIG. 6 is a schematic depiction of an annular conjunctival cover according to an example embodiment of the invention.

Referring now to FIG. 5, another embodiment of conjunctival cover 20 is depicted. Dual ring conjunctival cover 50 generally includes inner ring 52, outer ring 54, nasal cover portion 56 and temporal cover portion 58. Inner ring 52 approximates the corneal diameter being slightly larger or slightly smaller than the limbus. Outer ring 54 is larger than inner ring 52 and may be sized to extend partially or completely into fornices 44. Inner ring 52, outer ring 54, nasal cover portion 56 and temporal cover portion 58 together define arcuate openings 60. Arcuate openings 60 include superior arcuate opening 62 and inferior arcuate opening 64. Inner ring 52, outer ring 54, nasal cover portion 56 and temporal cover portion 58 may be integrally formed, for example, by a molding process or may be overmolded or otherwise assembled of separate structures.

Figure 7:
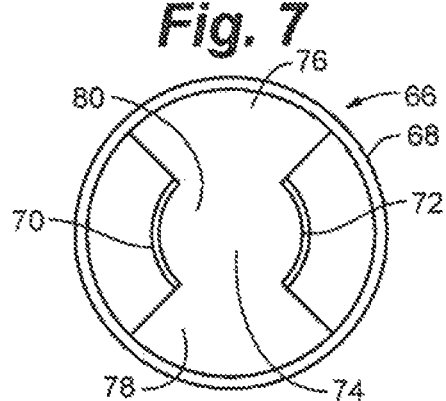
FIG. 7 is a schematic depiction of a conjunctival cover having a partial inner ring, an outer ring and a segmented structure according to an example embodiment of the invention.

Referring now to FIG. 7, another embodiment of conjunctival cover 20 is depicted. Partial inner ring conjunctival cover 66 generally includes outer ring 68, nasal inner ring segment 70, temporal inner ring segment 72, nasal cover portion 56 and temporal cover portion 58. These structure together define central opening 74 which includes superior opening portion 76, inferior opening portion 78 and central opening portion 80. Accordingly, when placed upon the eye, partial inner ring conjunctival cover 66 generally covers the nasal and temporal conjunctiva while not covering the superior and inferior conjunctiva which are covered by eyelids 36.

Conjunctival cover 20 may also include other fenestrations beyond those identified herein.

Figure 8:
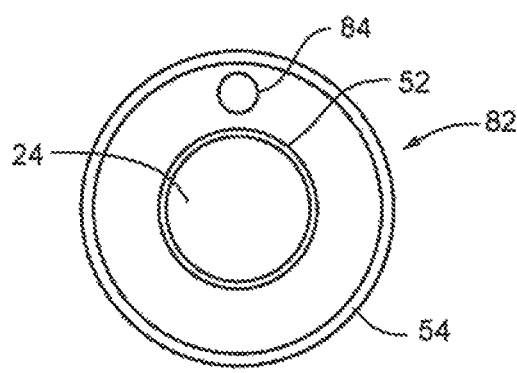
FIG. 8 is a schematic depiction of a conjunctival cover having a drug reservoir to support drug delivery capability according to an example embodiment of the invention.

Referring now to FIG. 8, another embodiment of conjunctival cover 20 is depicted. Drug delivery conjunctival cover 82 can be similar in structure to any of the above described conjunctival covers 20 but is adapted for drug delivery.

According to an embodiment depicted in FIG. 8, drug delivery conjunctival cover 82 includes first drug reservoir 84, second drug reservoir 86 and third drug reservoir 88. Drug delivery conjunctival cover 82 may include one or more drug reservoirs 90. Drug reservoirs 90 may be formed as cavities within drug delivery conjunctival cover 82 which are bounded by a material that is bio-absorbable or bio-degradable in the eye environment. A wall thickness of first drug reservoir 84, second drug reservoir 86 and third drug reservoir 88 may vary in order to facilitate timed release of drug dosages. The first drug reservoir may have a thinner wall that is breached by bio-absorption or biodegradation sooner than the thicker walls of second drug reservoir 86 or third drug reservoir 88.

Drug delivery conjunctival cover 82 may also be formed of a hydrophilic material that absorbs an aqueous solution of a drug to be released for later diffusion into the ocular conjunctival environment. Thus, drug delivery conjunctival cover 82 may be formed of a poly-HEMA or another hydrophilic material known to those skilled in the contact lens arts.

Figure 9:
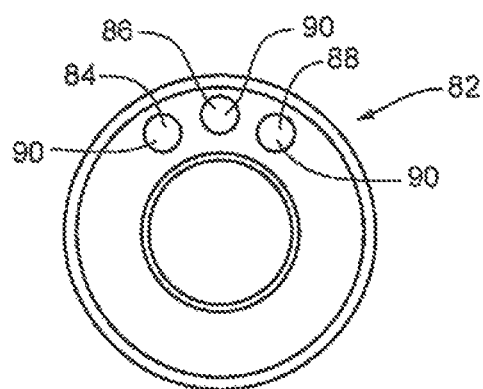
FIG. 9 is a schematic depiction of a conjunctival cover having multiple drug reservoirs to support drug delivery capability according to an example embodiment of the invention.
Figure 10:
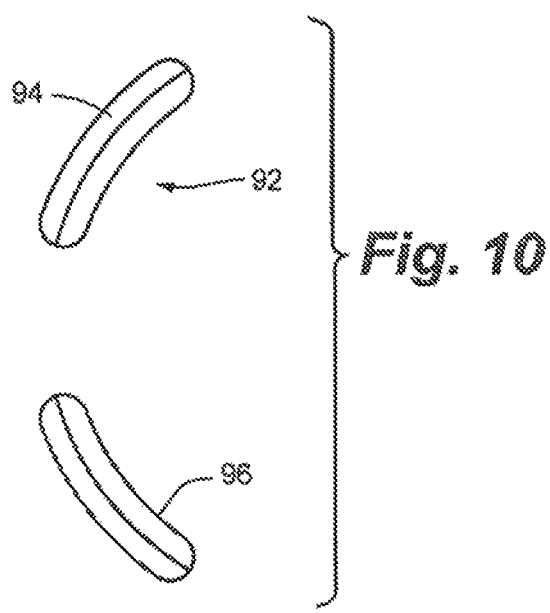
FIG. 10 is a schematic depiction of a conjunctival cover having multiple layers according to an example embodiment of the invention.
Figure 11:
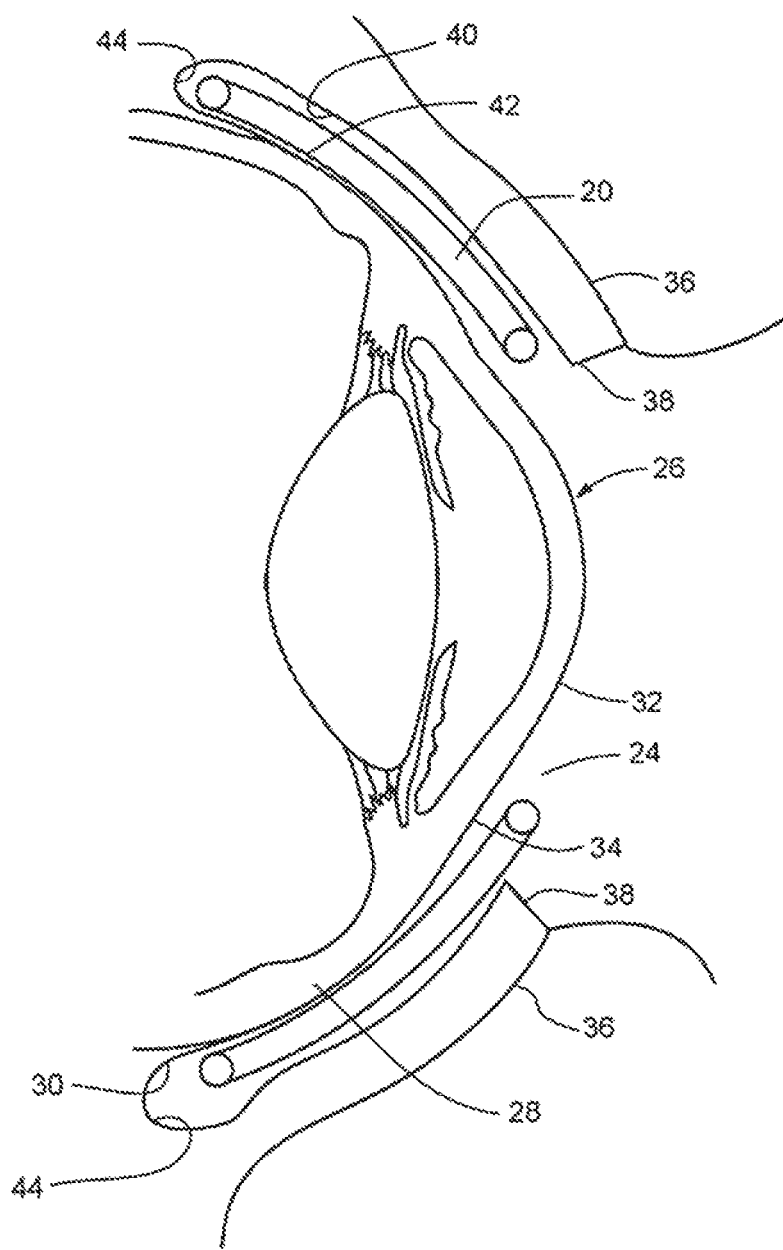
FIG. 11 is a schematic cross sectional view of a conjunctival cover applied to an eye according to an example embodiment of the invention.

Referring now to FIG. 9, another embodiment of conjunctival cover 20 is depicted in cross-section. Multi-layer conjunctival cover 92 includes at least first layer 94 and second layer 96. Multi-layer conjunctival cover 92 may have two or more layers of similar or different construction materials.

Drugs to be delivered by drug delivery conjunctival cover 82 may include but are not limited to antibiotics, steroids, glaucoma medications, antiviral medications, antifungal medications, NSAIDs, surface lubricants and anti-inflammatories such as cyclosporine.

Drug delivery conjunctival cover 82 may also be utilized to deliver nano-technology substances into the eye.

According to another example embodiment the invention includes a method of treating an eye, including applying an annular conjunctival cover to the eye by retracting the eyelids and placing the annular conjunctival cover on a bulbar conjunctiva of the eye while leaving a cornea of the eye substantially uncovered; and releasing the eye lids.

The method may further include incorporating a drug into the annular conjunctival cover prior to application.

The method may further include incorporating the drug into the annular conjunctival cover by exposing the annular conjunctival cover to the drug in solution or suspension such that the drug is absorbed into the annular conjunctival cover.

The method may further include incorporating the drug into the annular conjunctival cover by inserting the drug into a drug reservoir incorporated in the annular conjunctival cover.

The method may further include inserting multiple drugs into multiple separate drug reservoirs incorporated in the annular conjunctival cover.

In operation, various embodiments of conjunctival cover 20 are applied to conjunctiva 30 in a similar fashion to the application of a soft contact lens or a sclera contact lens. Various embodiments of conjunctival cover 20 may be applied to eye 26 by the patient or by a health care professional. Eyelids 36 are pulled open by using the fingers near the eyelids margins 38 and conjunctival cover 20 is placed upon the eye at least partially covering the conjunctiva 30. As discussed above, various embodiments of conjunctival cover 20 may partially or completely cover the conjunctiva 30 while partially or completely exposing the cornea 32. Various embodiments of conjunctival cover 20 trap mucin and other tear film components between conjunctival cover 20 and conjunctiva 30. The tear film also covers the external surface of conjunctival cover 20. Upon blinking, eyelids 36 and in particular eyelid margins 38 pass over conjunctival cover 20 and both wipes tear film components on the surface of conjunctival cover 20 onto cornea 32 and also squeezes or massages tear film components between conjunctival cover 20 and conjunctiva 30 onto cornea 32.

Elliptical conjunctival cover 46 covers conjunctiva 30 substantially between eyelid margins 38. Dual ring conjunctival cover 50 is placed on eye 26 so that nasal cover portion 56 covers nasal palpebral conjunctiva 40 while temporal cover portion 58 covers the temporal bulbar conjunctiva 42.

Partial inner ring conjunctival cover 66 is placed on eye 26 so that nasal cover portion 56 covers nasal bulbar conjunctiva 40 while temporal cover portion 58 covers temporal bulbar conjunctiva 42.

Drug delivery conjunctival cover 82 is placed on eye 26 where drugs absorb into drug delivery conjunctival cover 82 diffuse out into eye 26 and surrounding structures.

In the case of drug delivery conjunctival cover 82 having first drug reservoir 84 and optionally second drug reservoir 86 and third drug reservoir 88, drug reservoirs 90 dissolve at planned rate to provide time release of contained drugs into the eye.

The present invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method of treating an eye, comprising:
applying an annular conjunctival cover to the eye by placing the annular conjunctival cover on a conjunctiva of the eye, wherein the annular conjunctival cover comprises:
an annular curved shell having a conjunctival portion structured to conform to and overly at least part of the conjunctiva of an eye, the annular curved shell having an outer edge and an inner edge, the annular curved shell defining a central opening therethrough, the central opening being formed by the inner edge of the annular curved shell and sized to leave a cornea of the eye at least partially uncovered when the conjunctival cover is applied to the eye; and
at least one drug reservoir formed in the annular curved shell.

2. The method of claim 1, wherein the inner edge is circular, and wherein the central opening is sized to leave the cornea completely uncovered.

3. The method of claim 1, wherein the outer edge is sized to extend to the conjunctival fornices.

4. The method of claim 1, wherein the outer edge is elliptical and is sized to conform to a portion of the eye between lid margins of eyelids.

5. The method of claim 1, wherein the annular conjunctival cover further comprises a drug absorbed into the drug reservoir for delivery to the eye.

6. The method of claim 1, wherein the at least one drug reservoir comprises three drug reservoirs.

7. The method of claim 1, wherein at least a portion of the annular curved shell surrounding the at least one drug reservoir comprises a bioabsorbable or biodegradable material.

8. The method of claim 7, wherein the at least one drug reservoir comprises:

a first drug reservoir structured to release a first contained drug aliquot after a first time period; and a second drug reservoir structured to release a second contained drug aliquot after a second time period that is different from the first time period.

9. The method of claim 8, wherein the at least one drug reservoir further comprises a third drug reservoir structured to release a third contained drug aliquot after a third time period that is different from the first time period and the second time period.

10. The method of claim 8, wherein a first portion of the annular curved shell surrounding the first drug reservoir has a thinner wall than a second portion of the annular curved shell surrounding the second drug reservoir and a third portion of the annular curved shell surrounding the third drug reservoir.

11. The method of claim 1, wherein the annular curved shell comprises a first layer and a second layer.

12. The conjunctival cover of claim 11, wherein the first layer and the second layer are made of different materials, and wherein at least one of the different materials is structured to absorb a drug.

* * * * *